United States Patent
Hung

(10) Patent No.: US 10,192,899 B2
(45) Date of Patent: Jan. 29, 2019

(54) DISPLAY AND MANUFACTURE METHOD THEREOF

(71) Applicant: AU OPTRONICS CORPORATION, Hsin-chu (TW)

(72) Inventor: Shih-Hsing Hung, Hsin-chu (TW)

(73) Assignee: AU OPTRONICS CORPORATION, Hsin-Chu (TW)

( * ) Notice: Subject to any disclaimer, the term of this patent is extended or adjusted under 35 U.S.C. 154(b) by 0 days.

(21) Appl. No.: 15/373,841

(22) Filed: Dec. 9, 2016

(65) Prior Publication Data

US 2017/0229491 A1    Aug. 10, 2017

(30) Foreign Application Priority Data

Feb. 4, 2016 (TW) .............................. 105103875 A

(51) Int. Cl.
| | | |
|---|---|---|
| H01L 27/12 | (2006.01) | |
| H01L 27/32 | (2006.01) | |
| A61L 2/08 | (2006.01) | |
| A61L 9/20 | (2006.01) | |
| H01L 29/417 | (2006.01) | |

(Continued)

(52) U.S. Cl.
CPC .......... *H01L 27/1262* (2013.01); *A61L 2/088* (2013.01); *A61L 9/205* (2013.01); *H01L 27/124* (2013.01); *H01L 27/1296* (2013.01); *H01L 27/3276* (2013.01); *H01L 27/3297* (2013.01); *H01L 29/41733* (2013.01); *H01L 29/42384* (2013.01); *H01L 29/45* (2013.01); *H01L 29/4908* (2013.01); *H01L 27/3262* (2013.01); *H01L 51/5246* (2013.01); *H01L 2227/323* (2013.01)

(58) Field of Classification Search
CPC ................................ A61L 9/205; A61L 9/088
See application file for complete search history.

(56) References Cited

U.S. PATENT DOCUMENTS

| | | |
|---|---|---|
| 9,196,740 B2 | 11/2015 | Chou et al. |
| 2007/0132377 A1 | 6/2007 | Yamazaki |

(Continued)

FOREIGN PATENT DOCUMENTS

| | | |
|---|---|---|
| CN | 1858633 A | 11/2006 |
| CN | 101789443 A | 7/2010 |

(Continued)

OTHER PUBLICATIONS

Office Action issued by (TIPO) Intellectual Property Office, Ministry of Economic Affairs, R. O. C. dated Dec. 29, 2016 for Application No. 105103875, Taiwan.

(Continued)

*Primary Examiner* — Phat X Cao
*Assistant Examiner* — Diana C Vieira
(74) *Attorney, Agent, or Firm* — Tim Tingkang Xia, Esq.; Locke Lord LLP

(57) ABSTRACT

A display includes a first substrate, a second substrate, a plurality of pixels and a photo-catalyst layer. The plurality of pixels are disposed between the first substrate and the second substrate. The photo-catalyst layer is disposed above a surface of the second substrate facing the first substrate or above a surface of the first substrate facing the second substrate. Manufacturing methods of a display are additionally disclosed.

11 Claims, 19 Drawing Sheets

(51) Int. Cl.
  *H01L 29/49*   (2006.01)
  *H01L 29/45*   (2006.01)
  *H01L 29/423*  (2006.01)
  *H01L 51/52*   (2006.01)

(56) References Cited

U.S. PATENT DOCUMENTS

| | | | |
|---|---|---|---|
| 2008/0079360 A1* | 4/2008 | Kubota | H01L 51/5246 313/505 |
| 2011/0160047 A1* | 6/2011 | Masahasshi | B01J 21/063 502/216 |
| 2011/0193089 A1* | 8/2011 | Chou | H01L 29/7869 257/59 |
| 2012/0161132 A1* | 6/2012 | Yamazaki | H01L 27/1225 257/57 |
| 2013/0027857 A1* | 1/2013 | Jeong | G02F 1/133308 361/679.01 |

FOREIGN PATENT DOCUMENTS

| | | | |
|---|---|---|---|
| JP | 2012038647 A * | 2/2012 | F21V 15/00 |
| TW | M252224 U | 12/2004 | |
| TW | 200529446 A | 9/2005 | |
| TW | M348306 U | 1/2009 | |

OTHER PUBLICATIONS

Office Action issued by the State Intellectual Property Office of the Peoples Republic of China dated Sep. 20, 2018 for Application No. CN201610311484.0.

\* cited by examiner

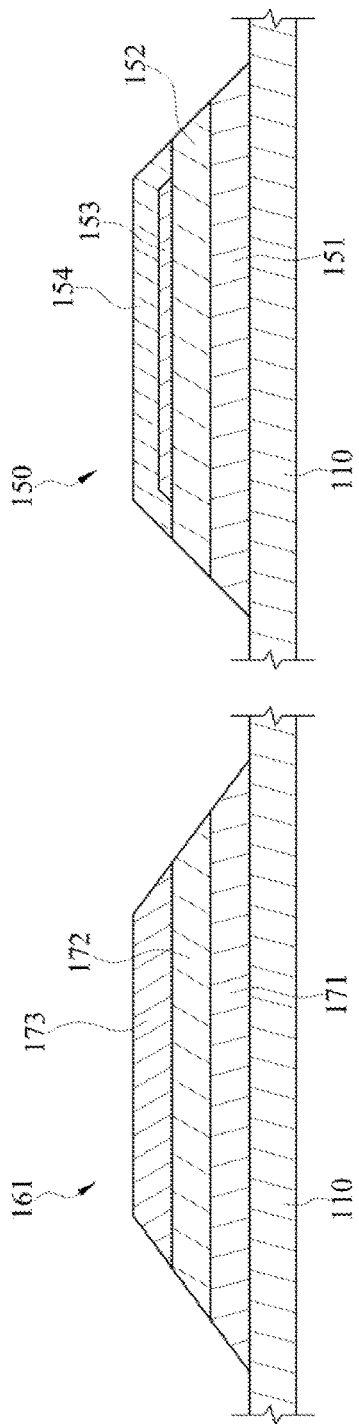

DISPLAY AND MANUFACTURE METHOD THEREOF

CROSS-REFERENCE TO RELATED PATENT APPLICATION

This application claims the benefit of priority to Taiwan Patent Application No. 105103875, filed Feb. 4, 2016. The entire content of the above identified application is incorporated herein by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD

The present embodiments relate to a display, and more specifically to a display with a photo-catalyst layer.

BACKGROUND

Applications on displays are increasingly popular. For example, currently, a display can be integrated with the functionalities of a camera, communication or displaying. However, with the rise of the awareness for environmental protection, inventions integrating the idea or functionality of environmental protection in a display are still sparse.

SUMMARY

Certain embodiments of the present invention provide a display, comprising a first substrate, a second substrate, a plurality of pixels, and a photo-catalyst layer. The plurality of pixels are disposed between the first substrate and the second substrate, and the photo-catalyst layer is disposed above a surface of the second substrate facing the first substrate or above a surface of the first substrate facing the second substrate.

In certain alternative embodiments, each of the pixels further comprises a transistor, and each of the transistors comprises a gate electrode, a source electrode, and an active layer. The photo-catalyst layer and the gate electrode or the photo-catalyst layer and the source electrode belong to the same film layer.

In certain alternative embodiments, the photo-catalyst layer comprises an oxide metal layer, and the gate electrode comprises a first gate metal layer. The oxide metal layer and the first gate metal layer belong to the same film layer.

In certain embodiments, the photo-catalyst layer further comprises a first metal layer. The oxide metal layer is stacked on the first metal layer and is an oxide of the first metal layer. The sum of a thickness of the oxide metal layer and a thickness of the first metal layer is less than a thickness of the first gate metal layer.

In certain alternative embodiments, the sum of the thickness of the oxide metal layer and the thickness of the first metal layer is greater than 0 nm and less than 100 nm.

In certain alternative embodiments, the gate electrode comprises a first gate metal layer, a second gate metal layer, and a third gate metal layer stacked in order; and the photo-catalyst layer comprises the oxide metal layer, the first metal layer, a second metal layer, and a third metal layer stacked in order; wherein the first gate metal layer and the first metal layer belong to the same film layer, the second gate metal layer and the second metal layer belong to the same film layer, and the third gate metal layer and the third metal layer belong to the same film layer.

In certain alternative embodiments, the display further comprises a light source, disposed at one side of the second substrate, and is configured for emitting UV light to the photo-catalyst layer.

Another embodiment of the present invention provides a manufacture method of a display. The method comprises: providing a first substrate; forming a gate electrode above the first substrate, and simultaneously forming an external metal layer above the first substrate; forming an insulating layer above the gate electrode to cover the gate electrode; and heating the external metal layer to make it form an oxide metal layer.

A further embodiment of the present invention provides another manufacturing method of a display. The method comprises: providing a first substrate; forming a gate electrode above the first substrate; forming an insulating layer above the gate electrode to cover the gate electrode; forming a source electrode and a drain electrode above the insulating layer, and simultaneously forming an external metal layer while forming the source electrode and/or the drain electrode; forming a protective layer above the source electrode and the drain electrode; and heating the external metal layer to make it form an oxide metal layer.

Corresponding to the two above-described methods, certain alternative embodiments further comprise forming a pixel electrode at a side of the gate electrode opposite to the first substrate, wherein heating the external metal layer occurs simultaneously with an annealing process of the pixel electrode.

The certain embodiments of the present invention disclose a display integrated with a photo-catalyst layer and a manufacturing method thereof, and provide a convenient display with the photo-catalyst layer and its efficacy.

The above description of the content of the present invention and the following illustration of the embodiments are intended to demonstrate and explain the spirit and principle of the present invention as well as to provide further explanations of claims of the present invention.

BRIEF DESCRIPTION OF THE DRAWINGS

FIGS. 6A to 6C are schematic drawings of detailed structures corresponding to the gate electrode and the photo-catalyst layer in FIGS. 5A to 5C respectively;

DETAILED DESCRIPTION

Figure 1:
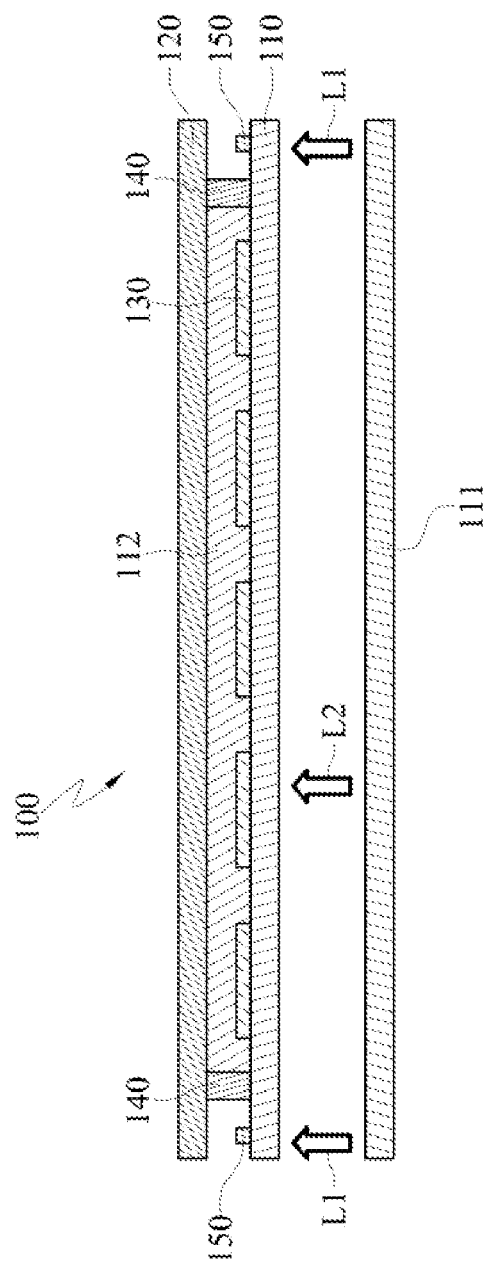
FIG. 1 is a cross-sectional drawing of a display according to an embodiment of the present invention.

The terms used in this specification generally have their ordinary meanings in the art of the context of the disclosure, and in the specific context where each term is used. Certain terms that are used to describe the disclosure are discussed below, or elsewhere in the specification, to provide additional guidance to the practitioner regarding the description of the disclosure. In addition, it should be appreciated that the same thing can be said in more than one way, with its meaning being understood as a selection for one of the multiple explanations or as a whole. Consequently, alternative language and synonyms may be used for any one or more of the terms discussed herein. Whether or not a term is elaborated or discussed herein, using alternative language and synonyms does not entail any specific meaning. Synonyms for certain terms are provided. A frequent use of one or more synonyms does not exclude the use of other synonyms. The use of examples in any of this specification, including examples of any terms discussed herein, is illustrative only, and in no way limits the scope and meaning of the disclosure or of any exemplified terms. Likewise, the disclosure is not limited to various embodiments given in this specification.

It will be understood that when an element is referred to as being (electrically) coupled to another element, it can be directly (electrically) coupled to the other element, or intervening elements may be present between them. In contrast, when an element is referred to as being directly (electrically) coupled to another element, no intervening elements are present. As used herein, the term "and/or" includes any and all combinations of one or more of the associated listed items.

It shall also be understood that in the description herein of signal transmission or provision, transmitted signals may be subjected to attenuation or distortion, but they still have a correspondence relation with those signals before transmission, and generally, the correspondence relation of two signals at a signal transmitting end and a signal receiving end is not eliminated due to attenuation or distortion generated in the transmission.

It shall also be understood that when an element is referred to as being located "on" another element, it can be directly located on the other element, or intervening elements may be present between them. In contrast, when an element is referred to as being located directly on another element, no intervening elements are present. As used herein, the term "and/or" includes any and all combinations of one or more of the associated listed items.

It will be understood that, although the terms "first", "second", and "third" etc. may be used herein to describe various elements, components, regions, layers and/or sections, these elements, components, regions, layers and/or sections should not be limited by these terms. These terms are only configured to distinguish one element, component, region, layer and/or section from another element, component, region, layer and/or section. Thus, a first element, component, region, layer and/or section discussed below could be termed a second element, component, region, layer and/or section without departing from the content of the disclosure.

The terminology used herein is for the purpose of describing particular embodiments only and is not intended to be limiting the disclosure. As used herein, the singular forms "a", "an" and "the" are intended to include the plural forms as well, unless the context clearly indicates otherwise. It will be further understood that when the terms "comprises" and/or "comprising", or "includes" and/or "including" or "has" and/or "having" are used in this specification, they specify the presence of stated features, regions, integers, steps, operations, elements, and/or components, but do not preclude the presence or addition of one or more of other features, regions, integers, steps, operations, elements, components, and/or groups thereof.

Further, relative terms, such as "below" or "bottom", "above" or "top", and "left" or "right" may be used herein to describe one element's relation to another as illustrated in the Figures. It will be understood that the relative terms are intended to encompass different orientations of the elements in addition to the orientation depicted in the Figures. For example, if elements were inverted with respect to the view in the Figures, element A, described as located "below" element B, for example, would now be located above element B. Thus, the exemplary term "below" can encompass both orientations of above and below. Similarly, if elements were inverted with respect to the view in the Figures, element A, described as located "beneath" or "under" element B, for example, would now be located "over" element B. Thus, the exemplary term "beneath" or "under" can encompass both orientations of over and under.

Unless otherwise defined, all the terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, indicating that the term "around", "about" or "approximately" can be inferred if not expressly stated.

Please refer to FIG. 1, a cross-sectional drawing of a display according to one embodiment of the present invention. A display 100 comprises a first substrate 110, a second substrate 120, a plurality of pixels 130, and a photo-catalyst layer 150. In addition, the display 100 may further comprise a display material 112, a light source 111, and a seal 140. The pixels 130 are disposed between the first substrate 110 and the second substrate 120, and the seal 140 generally or partially surrounds the plurality of pixels 130, thereby being encapsulated between the first substrate 110 and the second substrate 120 along with the first substrate 110 and the second substrate 120. The photo-catalyst layer 150 may be formed above a surface of the first substrate 110 facing the second substrate 120, or may also be formed above a surface of the second substrate 120 facing the first substrate 110. For example, in the present embodiment, the plurality of pixels 130 is disposed above a surface of the first substrate 110 facing the second substrate 120, and the corresponding photo-catalyst layer 150 is disposed above the surface of the first substrate 110 facing the second substrate 120. Alternatively, the plurality of pixels 130 may also be disposed on a surface of the second substrate 120 facing the first substrate 110, and the corresponding photo-catalyst layer 150 may be disposed on the surface of the second substrate 120 facing the first substrate 110. Generally, however, the photo-catalyst layer 150 and the pixels 130 are located at two opposite sides of the seal 140 respectively. The display material 112 is configured to be controlled by the pixels 130, thus changing its optical properties to result in changes in gray scale. For example, the display material 112 may be a liquid crystal material encapsulated within the seal 140, and the liquid crystal material is controlled by the field of the pixels 130, thus leading to different polarization properties. As another example, the display material 112 may be an OLED emitting material, which can receive the currents provided by the pixels 130 to generate different colors or intensities of light. The light source 111 may be used as a backlight source. In other words, in a non-emissive display (e.g., the liquid crystal display above), the light source 111 can be the backlight source of the display 100 that emits a light ray L2, and provide the light ray L2 to be controlled by the pixels 130 and the display material 112, thus the display 100 can produce different images. In addition, the light source 111 can also emit a UV light L1 (generally referring to a light ray having a wavelength of about 10 nanometer (nm) to 400 nm), so that the UV light L1 can stimulate the photo-catalyst layer 150, and thus the photo-catalyst layer 150 can be provided with the functionalities of sterilizing, deodorizing, and/or anti-molding.

Figure 2:
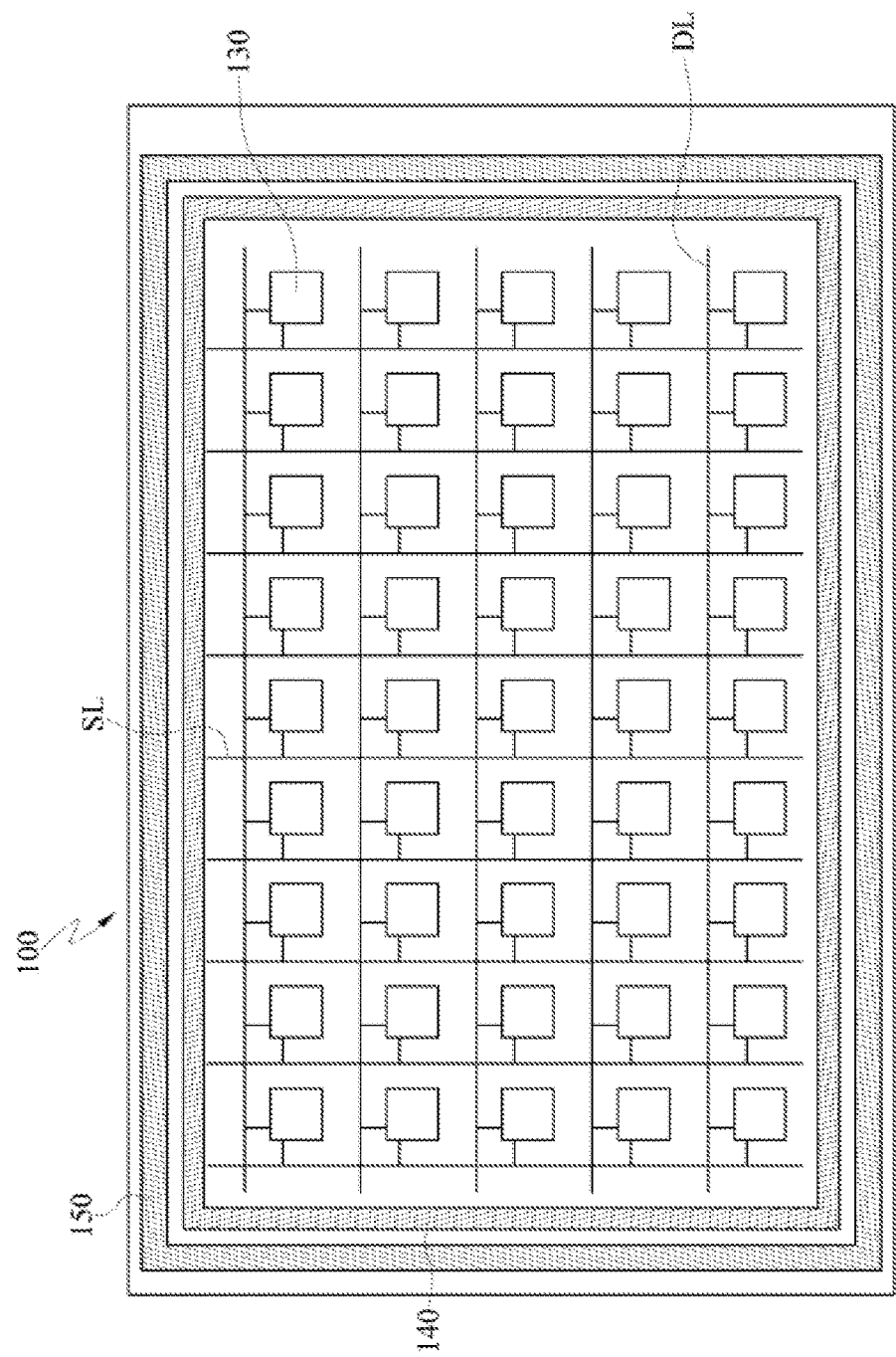
FIG. 2 is a front schematic drawing of a display according to an embodiment of the present invention.
Figure 12:
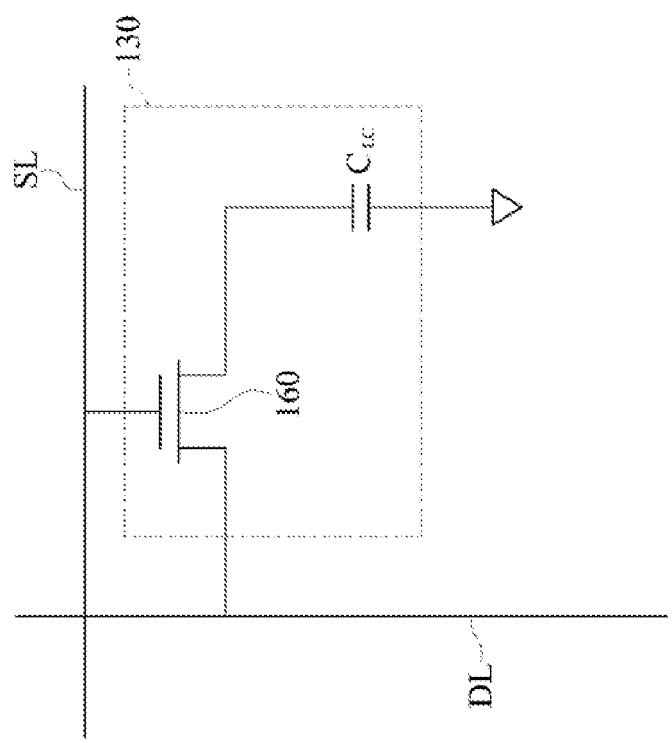
FIG. 12 is a circuit schematic diagram of liquid crystal pixels.

FIG. 2 is a front schematic drawing of a display according to an embodiment of the present invention. As described above, please refer to FIG. 2 in combination with FIG. 1, the display 100 comprises the first substrate 110, the second substrate 120, the plurality of pixels 130, the seal 140, and the photo-catalyst layer 150. The pixels 130 are arranged in a matrix, and the display 100 may further comprise a plurality of scan lines SLs and a plurality of data lines DLs. The scan lines SLs are electrically coupled to the corresponding pixels 130 to provide a scan signal to the pixels 130, enabling update actions of the scan signal of the pixels 130. The data lines DLs are electrically coupled to the corresponding pixels 130 to provide a desired data signal to the pixels 130, such that the pixels 130 receiving the data signal can exhibit certain gray scale according to the data signal. For example, please refer to FIG. 12, a circuit schematic diagram of liquid crystal pixels. The scan lines SLs can turn on a transistor 160 in the pixels, such that the pixels 130 can provide the data signal to a liquid crystal capacitor $C_{LC}$, thus controlling the liquid crystals to which the liquid crystal capacitor $C_{LC}$ corresponds.

Refer to FIG. 2 again. The seal 140 in FIG. 2 can substantially surround the region where the pixels 130 are arranged. The photo-catalyst layer 150 is located at the other side of the seal 140 opposite to the region where the pixels 130 are arranged, and the photo-catalyst layer 150 may substantially surround the seal 140. Accordingly, please refer to FIG. 3, a front schematic front drawing of a display according to another embodiment of the present invention.

Figure 3:
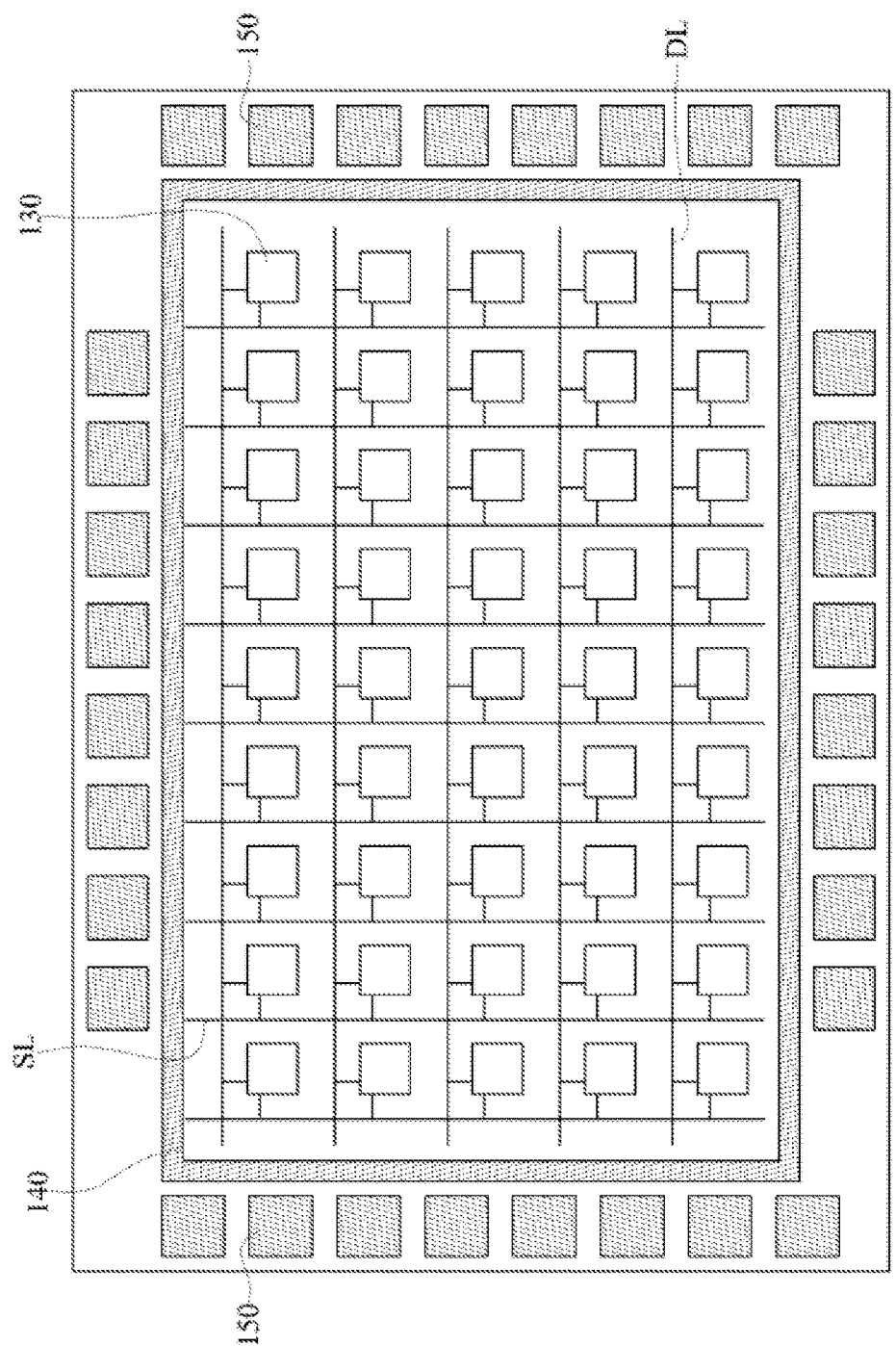
FIG. 3 is a front schematic drawing of a display according to another embodiment of the present invention.

FIG. 3 differs from FIG. 2 mainly in that the photo-catalyst layer 150 may be a plurality of separate blocks arranged around the seal 140 sequentially.

In the above embodiments, the photo-catalyst layer 150 may be formed on the surface of the first substrate 110 facing the second substrate 120, or may also be formed on the surface of the second substrate 120 facing the first substrate 110. In other words, the photo-catalyst layer 150 can be incorporated into the manufacturing process of a display structure of the display 100, and a peripheral region of the substrate can be appropriately utilized, achieving the convenient functionalities of a photo-catalyst in self-cleaning, sterilizing, deodorizing, and/or anti-molding.

Figure 4A:
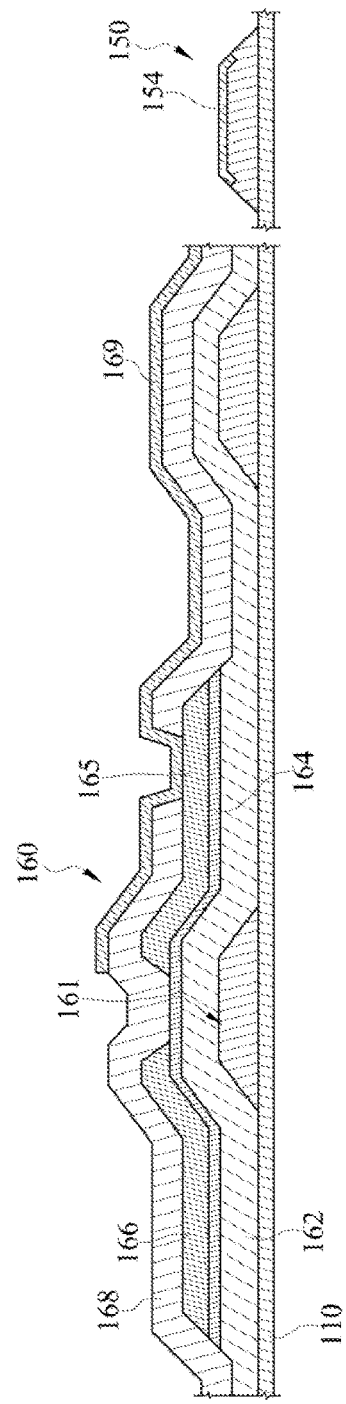
FIG. 4A is a cross-sectional schematic drawing of a pixel structure and a photo-catalyst layer according to an embodiment of the present invention.

Referring to FIG. 4A, a cross-sectional schematic view of a pixel structure and a photo-catalyst layer according to an embodiment of the present invention. Also referring to FIG. 4B, a schematic view of detailed structures of a gate electrode and a photo-catalyst layer according to an embodiment of the present invention. Although the present embodiment is described with an example in which the photo-catalyst layer 150 and the pixels 130 are formed on the surface of the first substrate 110 facing the second substrate 120, the photo-catalyst layer 150 and the pixels 130 may also be formed on the surface of the second substrate 120 facing the first substrate 110, and the structure and manufacturing method thereof are also similar to the technical solutions described below. The pixels 130 comprise the transistor 160 having a gate electrode 161, an active layer 164, a drain electrode 165, and a source electrode 166. The source electrode 166 and the drain electrode 165 are electrically coupled to two ends of the active layer 164 respectively, and are stacked on the active layer 164. The gate electrode 161 is configured to control the active layer 164, such that the source electrode 166 and the drain electrode 165 are substantially conducted or cut off. An insulating layer 162, insulating the active layer 164 from the gate electrode 161, is stacked on the gate electrode 161. A protective layer 168 is disposed above the active layer 164, the source electrode 166, and the drain electrode 165. The protective layer 168 is provided with a via. A pixel electrode 169 is disposed above the protective layer 168 for the drain electrode 165 to receive a voltage through the via, so as to control liquid crystal molecules or other display materials (not shown) disposed thereon. The photo-catalyst layer 150 is disposed at at least one side of the pixels 130, and in the present embodiment, the photo-catalyst layer 150 and the gate electrode 161 may belong to the same film layer. In other words, the photo-catalyst layer 150 and the gate electrode 161 may be defined by the same photo-mask, or each layer structure of the photo-catalyst layer 150 and the gate electrode 161 is defined by a corresponding photo-mask.

Figure 4B:
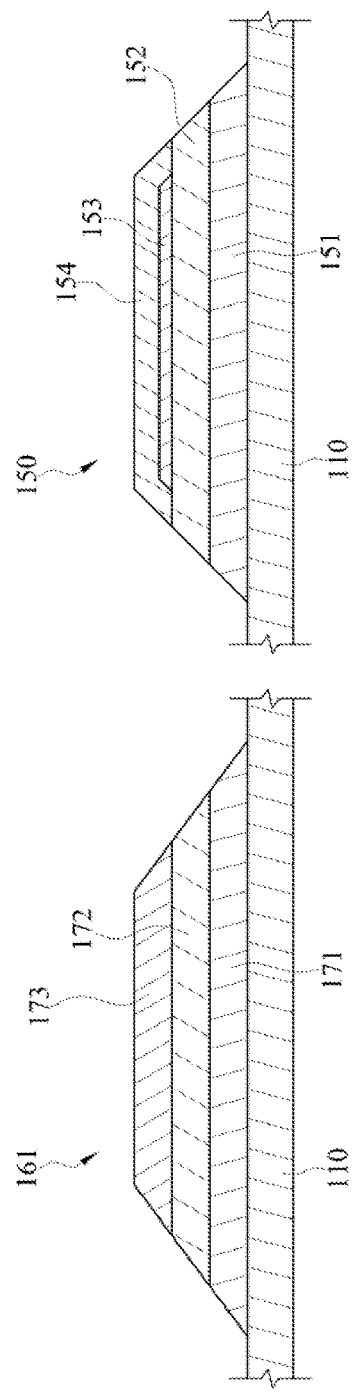
FIG. 4B is a schematic drawings of detailed structures of a gate electrode and a photo-catalyst layer according to an embodiment of the present invention.

The photo-catalyst layer 150 and the gate electrode 161 may be a stack of multi-layer metals and/or metal oxides respectively. Refer to FIG. 4B. For example, the gate electrode 161 comprises sequentially stacked titanium (Ti), aluminum (Al), and titanium (Ti) metals from a side proximal to the first substrate 110 to a side away from the first substrate 110. The photo-catalyst layer 150 comprises sequentially stacked titanium (Ti), aluminum (Al), titanium (Ti), and titanium dioxide (TiO2) from the side proximal to the first substrate 110 to the side away from the first substrate 110. The three-layer stacked structures of the gate electrode 161 and the photo-catalyst layer 150 may respectively belong to corresponding identical film layers sequentially from the side proximal to the first substrate 110 to the side away from the first substrate 110. In other words, they may be defined by the same photo-masks respectively. Further, the titanium metal layer and the titanium dioxide layer of the photo-catalyst layer 150 farthest from the first substrate 110 belong to the same film layer. In fact, the titanium dioxide layer is formed by oxidation of the titanium metal layer below it. In addition, the thickness of the photo-catalyst layer 150 may be less than that of the gate electrode 161 to facilitate the formation of titanium dioxide. The total thickness of titanium metal and titanium dioxide farthest from the first substrate 110 (i.e., the metal layer 153 plus the oxide metal layer 154) is less than the thickness of the titanium metal layer of the gate electrode farthest from the first substrate 110. For example, the total thickness of titanium metal and titanium dioxide farthest from the first substrate (i.e., the metal layer 153 plus the oxide metal layer 154) is less than 100 nm, such that the material of the titanium metal layer can be effectively utilized. Generally, since the photo-catalyst layer 150 is formed in the peripheral region of the substrate, a thinner thickness can be easily achieved in the process. In addition, this may also be achieved through a design of the photo-mask or various adjustments made for the certain regions in the process. In the process of oxidizing the titanium metal layer, a layer of titanium dioxide having a thickness of about 3 nm to 50 nm may be formed on a surface of the titanium metal layer. Therefore, a desired titanium dioxide layer can be effectively formed from the thinner titanium metal layer. More specifically, as shown in the figure, a metal layer 151, a metal layer 152, and the metal layer 153 are titanium (Ti), aluminum (Al), and titanium (Ti) metals respectively, and a gate metal layer 171, a gate metal layer 172, and a gate metal layer 173 are titanium (Ti), aluminum (Al), and titanium (Ti) metals respectively. The oxide metal layer 154 is titanium dioxide ($TiO_2$).

Specifically, a material of the active layer 164 is, for example, or includes, for example, metal oxide semiconductor, amorphous silicon, polycrystalline silicon, low temperature poly-silicon, epitaxial silicon, organic semiconductor, and other suitable semiconductor material, or a stacked layer of at least two of the above-mentioned materials. The metal oxide semiconductor may be indium tin oxide (ITO), indium zinc oxide (IZO), aluminum tin oxide (ATO), aluminum zinc oxide (AZO), indium gallium oxide (IGO), indium germanium zinc oxide (IGZO), or another suitable metal oxide. Materials of the source electrode 166 and the drain electrode 165 are, for example, or include, for example, metal materials, other conductive materials, or stacked layers of metal materials and other conductive materials. The metal materials may be aluminum, copper, molybdenum, or titanium, and other conductive materials may be alloy, metal nitrides, metal oxides, metal oxynitrides, or other suitable materials. A material of the gate electrode 161 is, for example, or includes, for example, a metal material, another conductive material, or a stacked layer of a metal material and another conductive material. The metal material may be aluminum, copper, molybdenum, or titanium, and another conductive material may be alloy, metal nitride, metal oxide, metal oxynitride, or another suitable material. A material of the protective layer 168 is, or includes, for example, silicon oxide, silicon nitride, silicon oxynitride, or another dielectric material. A material of the pixel electrode 169 is or includes, for example, indium tin oxide (ITO), or indium zinc oxide (IZO). The transistor 160 can be a thin film transistor having a top gate, a bottom gate or even both a top gate and a bottom gate.

Figure 5A:
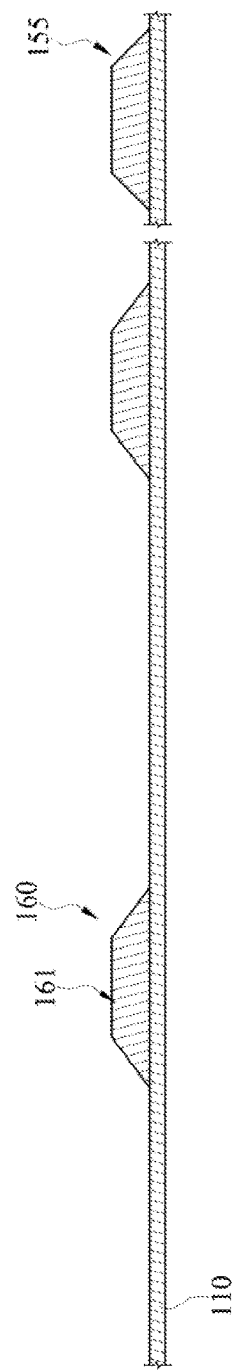
FIGS. 5A to 5C are schematic flow charts of a manufacturing method of a display according to an embodiment of the present invention.
Figure 5B:
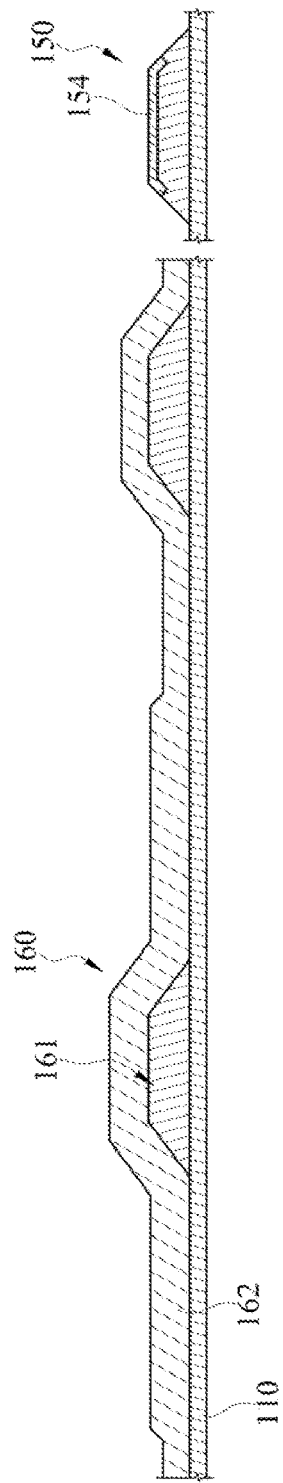
Figure 5C:
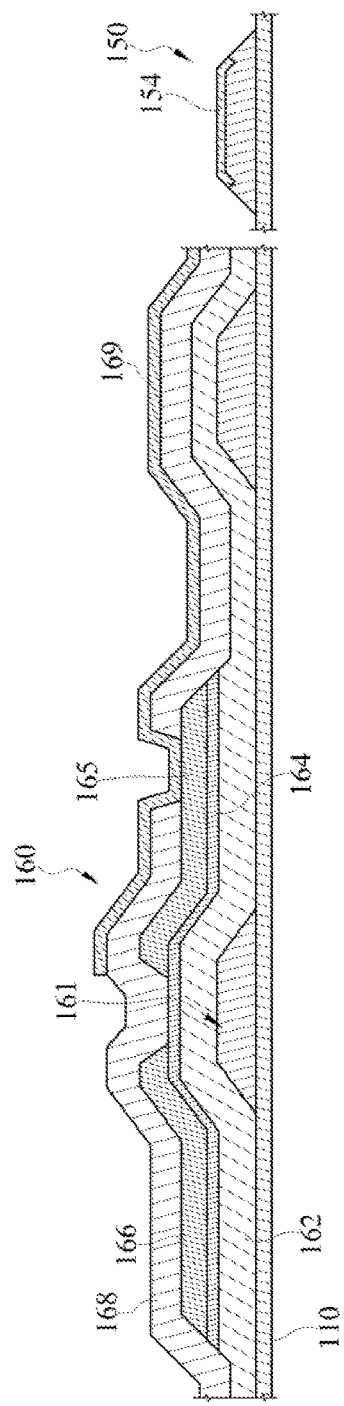
Figure 6A:
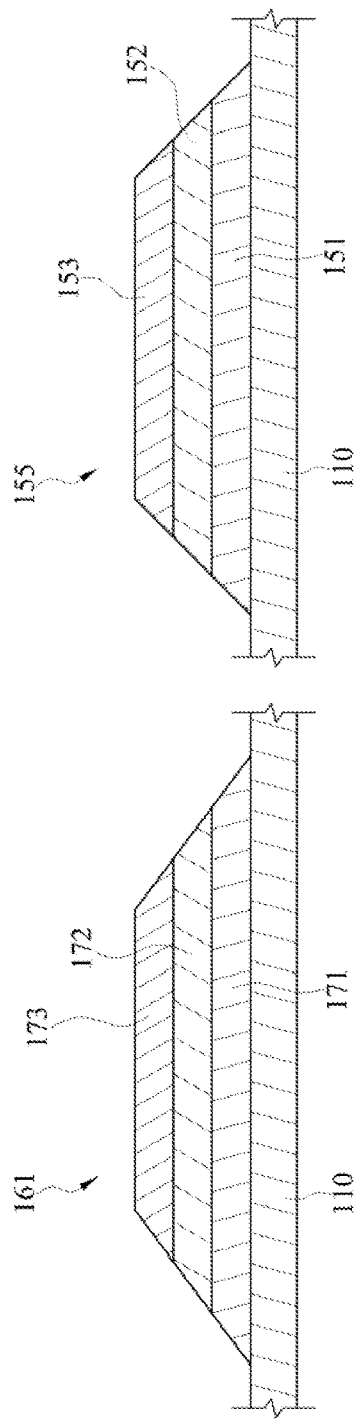
Figure 6C:
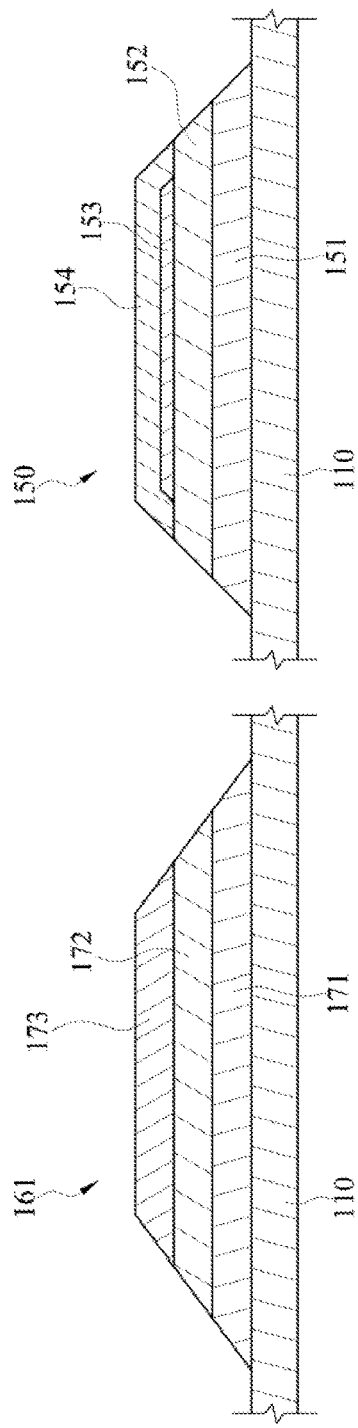
Figure 9:
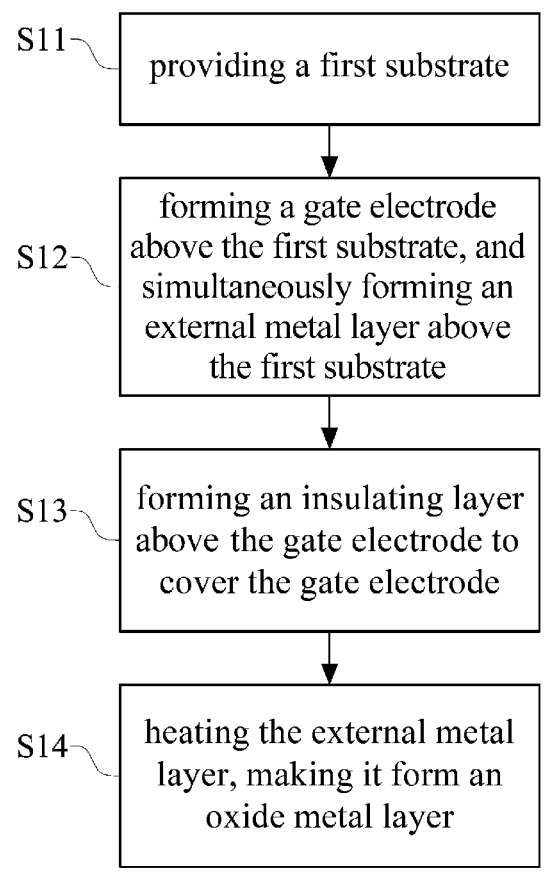
FIG. 9 is a flow chart of a first manufacturing method of a display according to an embodiment of the present invention.

Refer to FIG. 5A and FIG. 5C. FIGS. 5A to 5C are schematic flow charts of a manufacturing method of a display according to an embodiment of the present invention. Also referring to FIGS. 6A to 6C, schematic drawings of detailed structures corresponding to the gate electrode and the photo-catalyst layer in FIGS. 5A to 5C respectively. Referring to FIG. 9, a flow chart of a first manufacturing method of a display according to an embodiment of the present invention. The following steps are disclosed in FIG. 9:

S11: providing the first substrate 110;

S12: forming the gate electrode 161 above the first substrate 110, and simultaneously forming an external metal layer 155 above the first substrate 110;

S13: forming the insulating layer 162 above the gate electrode 161 to cover the gate electrode 161; and S14: heating the external metal layer 155, making it form the oxide metal layer 154.

Referring to FIG. 5A, the gate electrode 161 is formed above the first substrate 110, and simultaneously, the external metal layer 155 is formed above the first substrate 110. The simultaneous formation at this step means that the gate electrode 161 and the external metal layer 155 are defined by the same photo-mask, and not necessarily completely overlapped in time. Certainly, the above-described steps may also be done within the same time range, for example, simultaneously by the way of depositing, sputtering, or coating. Further, as described above and as shown in FIG. 6A, the gate electrode 161 and the external metal layer 155 each may have a multilayer stacked structure of metals. The gate electrode 161 may be made by forming titanium, aluminum, and titanium metal layers (the gate metal layer 171 to the gate metal layer 173) sequentially, and the external metal layer 155 may also be formed by forming titanium, aluminum, and titanium metal layers (the metal layer 151 to the metal layer 153) sequentially.

Referring to FIG. 5B, which corresponds to step S13 and step S14. The insulating layer 162 is formed above the first substrate 110 and the gate electrode 161 is covered by the insulating layer 162, so as to avoid the oxidation of the gate electrode 161 while heating the external metal layer 155 (e.g., annealing), resulting in variation of electrical characteristics in the gate electrode 161. After the insulating layer 162 covering the gate electrode 161 is formed, the external metal layer 155 may then be heated. The heating process may be an overall heating for the display panel or only a local heating. The heating temperature generally may be 20° C. to 300° C., for example, 20° C., 100° C., 200° C., and 300° C. As such, a certain thickness of an oxide can be generated above a surface of the external metal layer. The oxide generally is the oxide metal layer 154 formed by the oxidation of the metal layer 153 of the external metal layer 155 farthest from the first substrate 110; for example, the oxidation of titanium metal forms titanium dioxide. Certainly the metal layer of the external metal layer 155 farthest from the first substrate 110 may also be of another material having photo-catalyst properties after being oxidized, such as zinc (Zn) or nickel (Ni), which are oxidized into zinc oxide (ZnO) and nickel oxide (NiO) respectively. The photo-catalyst layer 150 is formed after the external metal layer 155 is subjected to the oxidation. In this case, it generally has a structure of the three metal layers 151, 152, 153 and the oxide metal layer 154 stacked on each other; for example, titanium, aluminum, titanium, and titanium dioxide stacked on each other. Through the above-mentioned formation process of the photo-catalyst layer, an additional step may not be required to form a photo-catalyst layer, or the number of steps required for additionally forming a photo-catalyst layer may be reduced.

Next, referring to FIG. 5C. The steps depicted in FIG. 5C are sequentially forming the active layer 164, the source electrode 166 and the drain electrode 165, the protective layer 168, and the pixel electrode 169 above the insulating layer 162. In this step, as shown in FIG. 5C, the photo-catalyst layer 150 and the gate electrode 161 have no substantial changes.

Figure 10:
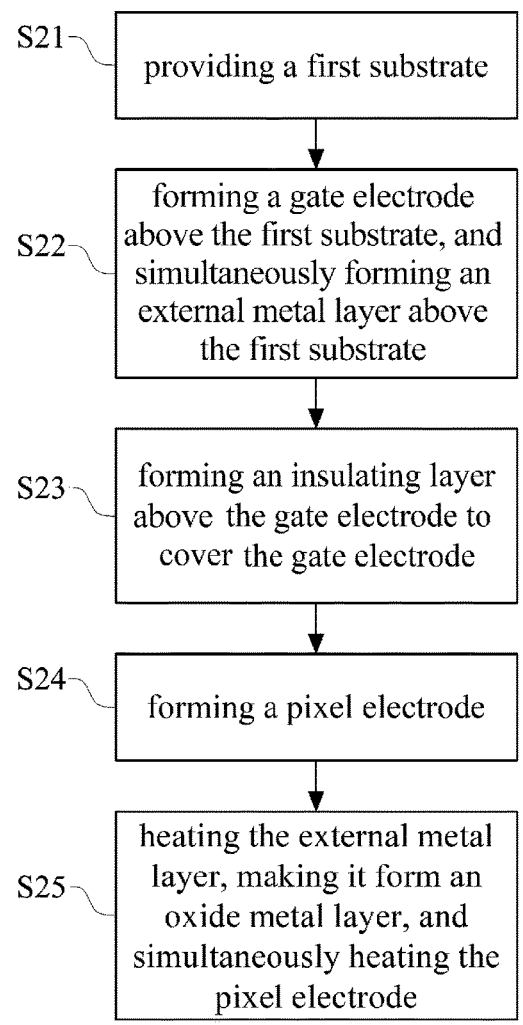
FIG. 10 is a flow chart of a second manufacturing method of a display according to an embodiment of the present invention.

Referring to FIG. 10, a flow chart of a second manufacturing method of a display according to an embodiment of the present invention. The following steps are disclosed in FIG. 10:

S21: providing the first substrate 110;

S22: forming the gate electrode 161 above the first substrate 110, and simultaneously forming the external metal layer 155 above the first substrate 110;

S23: forming the insulating layer 162 above the first substrate 110 to cover the gate electrode 161;

S24: forming the pixel electrode 169 before heating the external metal layer 155; and S25: heating the external metal layer 155, making it form the oxide metal layer 154, and simultaneously heating the pixel electrode 169.

The present manufacturing method differs from the first manufacturing method of a display in that the pixel electrode 169 is formed in advance, and the external metal layer 155 is concurrently heated using the annealing/heating process of the pixel electrode 169. Accordingly, an additional heating/annealing step may further be omitted in the present manufacturing method of a display.

Figure 7A:
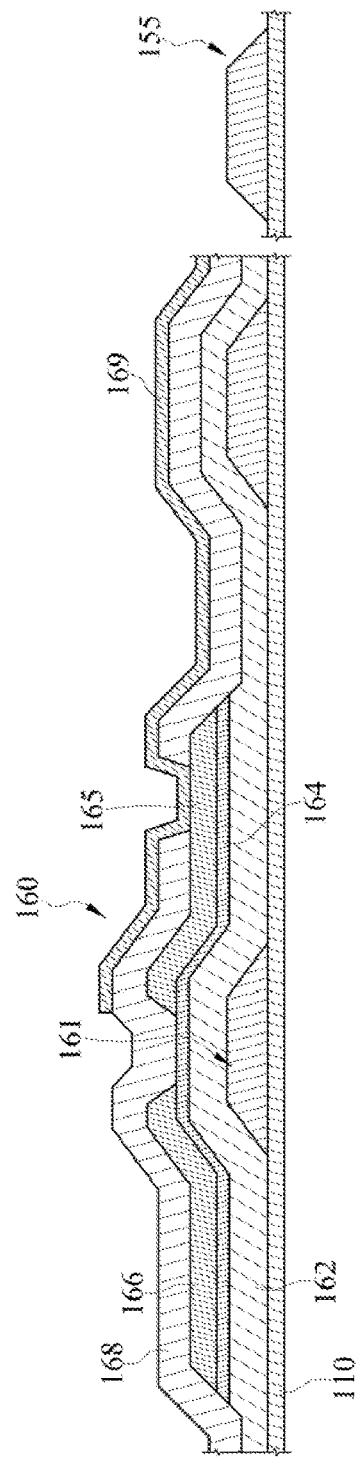
FIGS. 7A and 7B are schematic drawings of another manufacturing method according to an embodiment of the present invention.
Figure 7B:
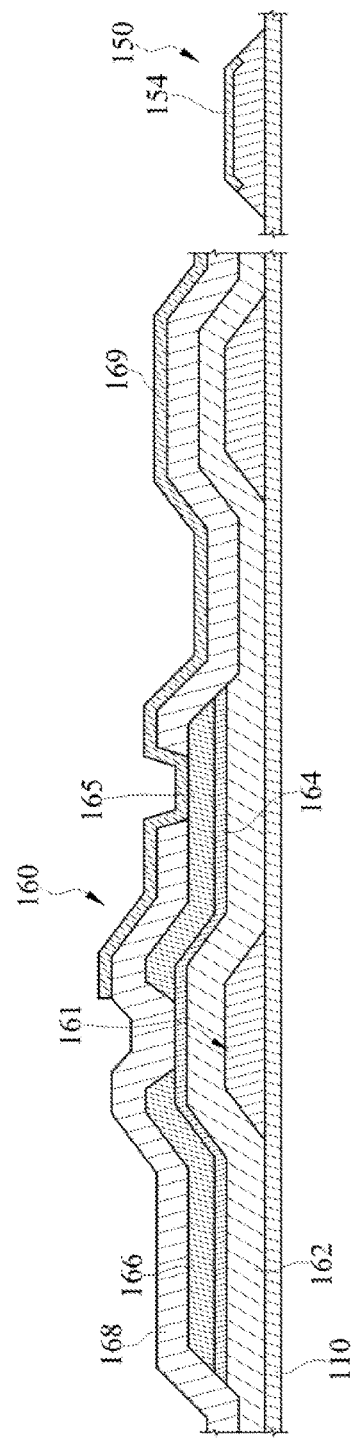
Figure 8A:
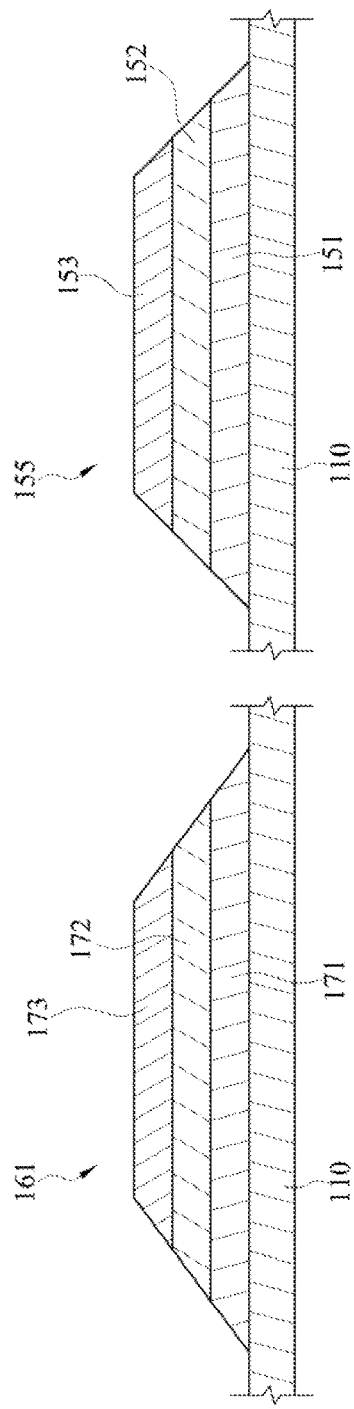
FIGS. 8A and 8B are schematic drawings of detailed structures corresponding to the gate electrode and the photo-catalyst layer in FIGS. 7A and 7B respectively.
Figure 8B:
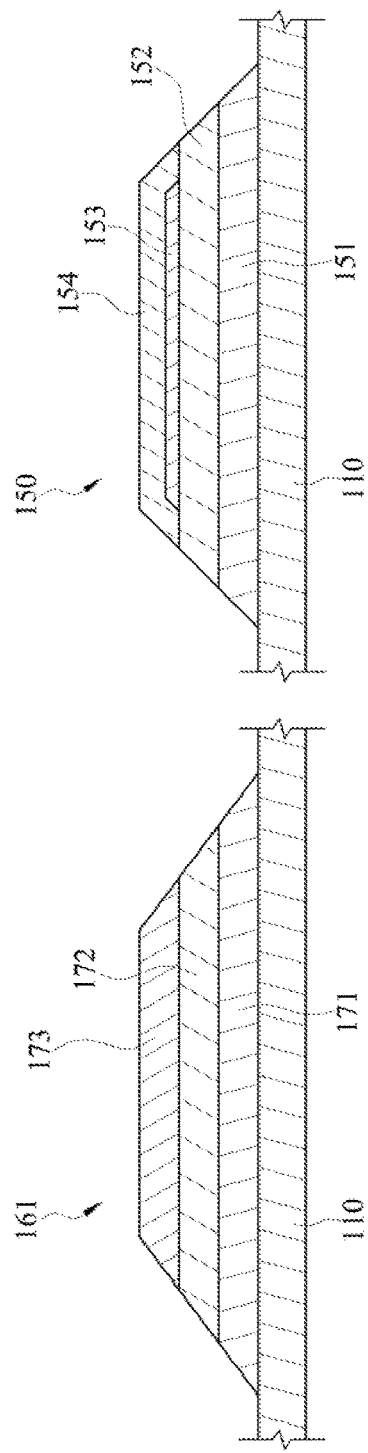

Referring to FIGS. 7A and 7B, schematic drawings of the process flow of another manufacturing method according to an embodiment of the present invention. As shown in FIG. 7A, the external metal layer 155 remains in a state of not being heated and thus not oxidized, after the pixel electrode 169 is formed. As shown in FIG. 7B, through the simultaneous annealing/heating process with the pixel electrode 169, as described for the first manufacturing method, the surface of the external metal layer 155 is oxidized to form the oxide metal layer 154, thus forming the photo-catalyst layer 150. The detailed structures of the gate electrode 161 and the photo-catalyst layer 150 in FIG. 7A and FIG. 7B are depicted in FIG. 8A and FIG. 8B respectively. FIGS. 8A and 8B are schematic drawings of detailed structures corresponding to the gate electrode and the photo-catalyst layer in FIGS. 7A and 7B respectively.

Figure 11:
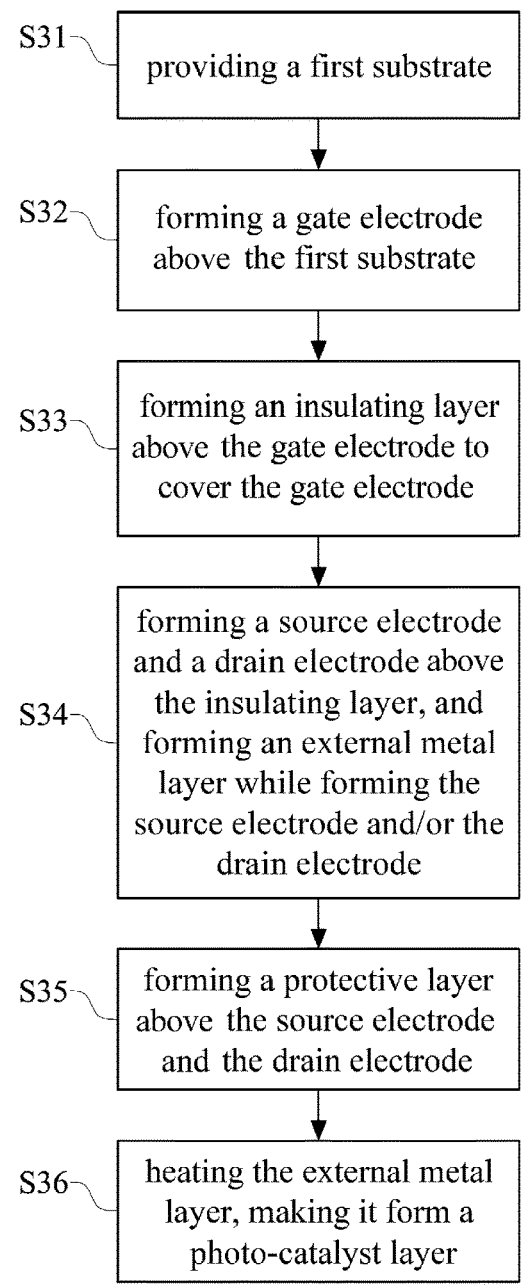
FIG. 11 is a flow chart of a third manufacturing method of a display according to an embodiment of the present invention.

Referring to FIG. 11, a flow chart of a third manufacturing method of a display according to an embodiment of the present invention. The following steps are disclosed in FIG. 11:

S31: providing the first substrate 110;

S32: forming the gate electrode 161 above the first substrate 110;

S33: forming the insulating layer 162 above the gate electrode 161 to cover the gate electrode 161;

S34: forming the source electrode 166 and the drain electrode 165 above the insulating layer 162, and simultaneously forming the external metal layer 155 while forming the source electrode 166 and/or the drain electrode 165;

S35: forming the protective layer 168 above the source electrode 166 and the drain electrode 165; and S36: heating the external metal layer 155, making it form the photo-catalyst layer 150.

In the steps disclosed by FIG. 11, the external metal layer 155 (i.e. a precursor of the oxide metal layer 150) may belong to the same film layer with the source electrode 166 and/or the drain electrode 165, thus also avoiding one additional step. In addition, step S36 of heating the external metal layer 155 to make it form the oxide metal layer 150 may also be preceded by the formation of the pixel electrode 169, and the external metal layer 155 can then be concurrently heated using the annealing/heating process of the pixel electrode 169.

The certain embodiments disclose a display integrated with a photo-catalyst layer and a manufacturing method thereof, and provide a convenient display with the photo-catalyst layer and its efficacy.

While the present invention has been disclosed with the above embodiments, these embodiments are not intended to limit the present invention. All alterations and modifications fall within the protection scope of the invention, without departing from the spirit and scope of the invention. Regarding the protection scope defined by the scope of the present invention, refer to the appended claims.

What is claimed is:

1. A display, comprising:
    a first substrate;
    a second substrate;
    a plurality of pixels, disposed between the first substrate and the second substrate;
    a seal disposed between the first substrate the second substrate; and
    a photo-catalyst layer, disposed above a surface of the second substrate facing the first substrate or above a surface of the first substrate facing the second substrate, wherein the photo-catalyst layer and the plurality of pixels are located at two opposite sides of the seal respectively;
    wherein each of the plurality of pixels comprises a transistor, and each of the transistors comprises a gate electrode, a source electrode, and an active layer, wherein the photo-catalyst layer and the gate electrode, or the photo-catalyst layer and the source electrode are belonging to a same first film layer.

2. The display of claim 1, wherein the photo-catalyst layer comprises an oxide metal layer, the gate electrode comprises a first gate metal layer, and the oxide metal layer and the first gate metal layer belong to a same second film layer.

3. The display of claim 2, wherein the display further comprises a light source, disposed at one side of the second substrate and configured to emit UV light on the photo-catalyst layer.

4. The display of claim 2, wherein the photo-catalyst layer further comprises a first metal layer, the oxide metal layer is stacked above the first metal layer and is an oxide of the first metal layer, and a sum of a thickness of the oxide metal layer and a thickness of the first metal layer is less than a thickness of the first gate metal layer.

5. The display of claim 4, wherein the display further comprises a light source, disposed at one side of the second substrate and configured to emit UV light on the photo-catalyst layer.

6. The display of claim 4, wherein the sum of the thickness of the oxide metal layer and the thickness of the first metal layer is greater than 0 nm and less than 100 nm.

7. The display of claim 4, wherein the gate electrode comprises the first gate metal layer, a second gate metal layer, and a third gate metal layer stacked in order; and
    the photo-catalyst layer comprises the oxide metal layer, the first metal layer, a second metal layer, and a third metal layer stacked in order;
    wherein the first gate metal layer and the first metal layer belong to the same second film layer; the second gate metal layer and the second metal layer belong to a same third film layer, and the third gate metal layer and the third metal layer belong to a same fourth film layer.

8. The display of claim 1, wherein the display further comprises a light source, disposed at one side of the second substrate and configured to emit UV light on the photocatalyst layer.

9. A manufacturing method of a display, comprising:
providing a first substrate;
forming a gate electrode above the first substrate, and simultaneously forming an external metal layer above the first substrate;
forming an insulating layer above the gate electrode to cover the gate electrode;
heating the external metal layer, and making it form an oxide metal layer; and
forming a pixel electrode at a side of the gate electrode opposite to the first substrate, wherein heating the external metal layer occurs simultaneously with an annealing process of the pixel electrode.

10. A manufacturing method of a display, comprising:
providing a first substrate;
forming a gate electrode above the first substrate;
forming an insulating layer above the gate electrode to cover the gate electrode;
forming a source electrode and a drain electrode above the insulating layer, and simultaneously forming an external metal layer while forming at least one of the source electrode and the drain electrode;
forming a protective layer above the source electrode and the drain electrode; and
heating the external metal layer, and making it form an oxide metal layer.

11. The manufacturing method of the display of claim 10, wherein the method further comprises forming a pixel electrode at a side of the gate electrode opposite to the first substrate, wherein heating the external metal layer occurs simultaneously with an annealing process of the pixel electrode.

* * * * *